(12) United States Patent
Jones

(10) Patent No.: US 8,303,595 B2
(45) Date of Patent: Nov. 6, 2012

(54) ROD REDUCTION DEVICE

(75) Inventor: Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 44 days.

(21) Appl. No.: 12/996,883

(22) PCT Filed: Jun. 11, 2009

(86) PCT No.: PCT/US2009/047011
§ 371 (c)(1),
(2), (4) Date: Dec. 8, 2010

(87) PCT Pub. No.: WO2009/152308
PCT Pub. Date: Dec. 17, 2009

(65) Prior Publication Data
US 2011/0087298 A1    Apr. 14, 2011

Related U.S. Application Data

(60) Provisional application No. 61/131,647, filed on Jun. 11, 2008.

(51) Int. Cl.
A61B 17/88    (2006.01)
(52) U.S. Cl. .......................... 606/86 A; 606/99
(58) Field of Classification Search ............... 606/86 A, 606/99, 264–275, 279
See application file for complete search history.

(56) References Cited

U.S. PATENT DOCUMENTS

| 5,720,751 | A | 2/1998 | Jackson |
| 6,123,707 | A | 9/2000 | Wagner |
| 6,957,758 | B2 | 10/2005 | Aranyi |
| 2002/0052603 | A1 | 5/2002 | Nichols et al. |
| 2004/0267275 | A1 | 12/2004 | Cournoyer et al. |
| 2006/0025769 | A1 | 2/2006 | Dick et al. |
| 2006/0074418 | A1* | 4/2006 | Jackson ............ 606/61 |
| 2006/0271050 | A1 | 11/2006 | Piza Vallespir |
| 2007/0093817 | A1 | 4/2007 | Barrus et al. |
| 2007/0213716 | A1 | 9/2007 | Lenke et al. |
| 2007/0270811 | A1 | 11/2007 | Dewey |
| 2007/0270867 | A1 | 11/2007 | Miller et al. |
| 2007/0282337 | A1 | 12/2007 | Garamszegi |
| 2008/0015601 | A1 | 1/2008 | Castro et al. |

OTHER PUBLICATIONS

International Search Report and Written Opinion issued by the U.S. Searching Authority in counterpart PCT Application No. PCT/US2009/047011, completed Jul. 29, 2009; mailed Aug. 12, 2009; 7 pages.

* cited by examiner

Primary Examiner — Ellen C Hammond
(74) Attorney, Agent, or Firm — Carter, DeLuca, Farrell & Schmidt, LLP

(57) ABSTRACT

A rod reduction device includes a rod reducing member, an anchoring member, and a sleeve. The rod reducing member is configured to engage a spinal rod. The anchoring member is configured to removably attach to a bone anchor. The sleeve defines a longitudinal axis and is operably associated with the rod reducing member and the anchoring member. The sleeve is rotatable with respect to the anchoring member for longitudinally translating the rod reducing member relative to the anchoring member.

18 Claims, 6 Drawing Sheets

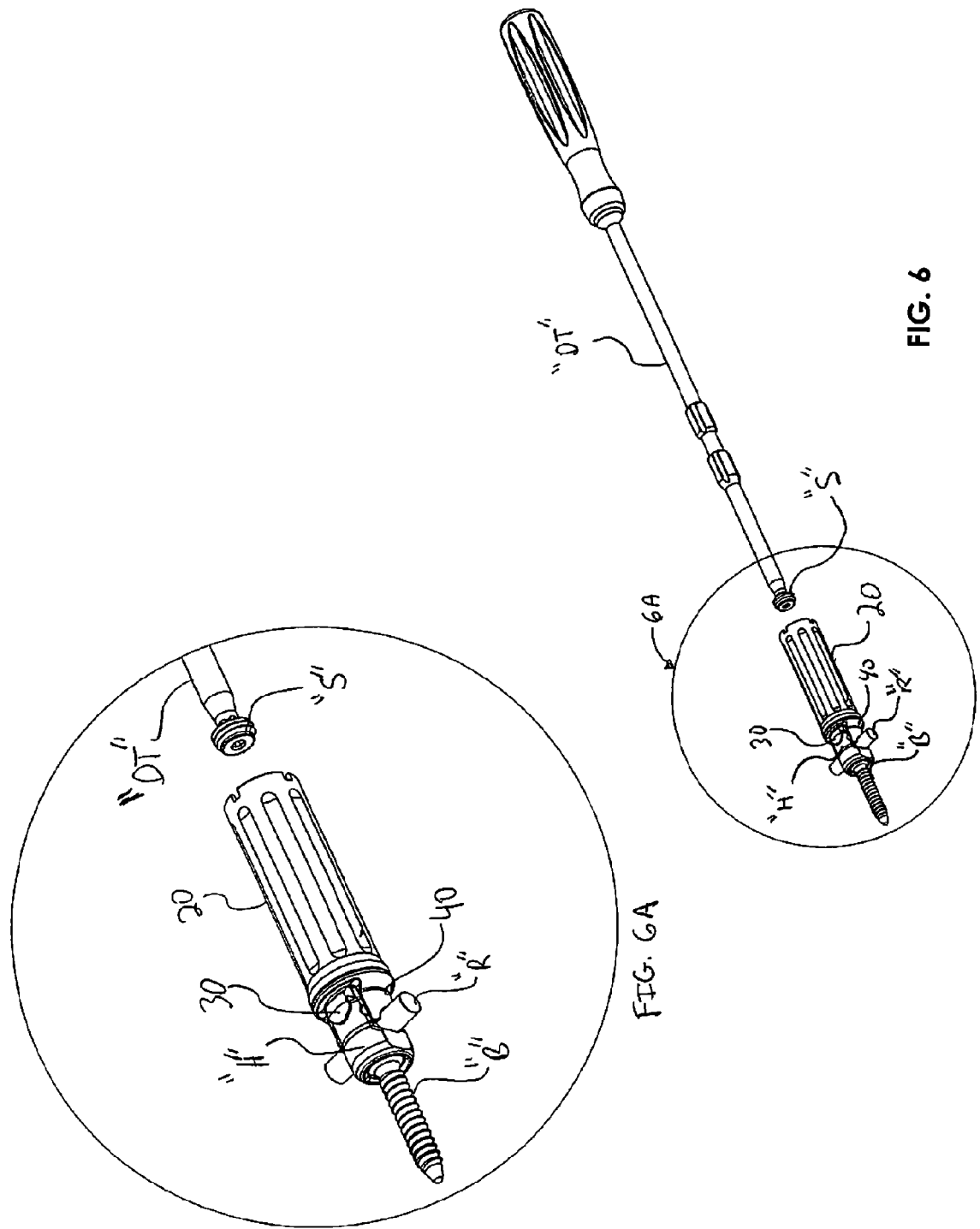

ROD REDUCTION DEVICE

CROSS-REFERENCE TO RELATED APPLICATIONS

The present application is a National Stage Entry of PCT/US2009/047011, which was filed Jun. 11, 2009, and claims the benefit of U.S. Provisional Application No. 61/131,647, which was filed Jun. 11, 2008, the entire contents of which are incorporated herein by reference.

BACKGROUND

1. Technical Field

The present disclosure relates to orthopedic surgery devices for stabilizing and fixing the bones and joints of the body. Particularly, the present disclosure relates to a manually operated device for reducing a spinal rod into a bone anchor in a controlled, measured manner.

2. Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions.

There are various disorders, diseases and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or all of the intervertebral disc to form a rigid column of bone, which is stabilized by mechanical hardware.

The mechanical hardware used to immobilize the spinal column typically involves a series of bone screws/anchors and metal rods or plates. When the spine surgery is performed posteriorly, it is common practice to place bone anchors into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone anchor and then securing that connecting rod in place can often require that the surgeon use a number of instruments and expend a great deal of time and effort. When bone anchors in several adjacent vertebrae are to be securely connected by a spinal rod, the repeated process of inserting the rod into the heads of the bone anchors and then securing the rod in place for each respective bone anchor can be difficult, tiresome and time consuming. Further, the alignment of the rod as it connects to each of the sequential bone anchors may require adjustment during the procedure and, therefore it is necessary that a device and method be provided by which the rod can be reduced into the head of each of the sequentially aligned bone anchors and, as necessary, easily adjusted so as to facilitate the process for the surgeon with minimal effort and loss of time.

SUMMARY

The present disclosure is directed to a rod reduction device including a sleeve, an anchoring member, and a rod reducing member. The sleeve defines a longitudinal axis and is operably associated with the rod reducing member and the anchoring member. The sleeve is operable with respect to the anchoring member for longitudinally translating the rod reducing member relative to the anchoring member. The sleeve may be configured to rotate independent of the rod reducing member. The proximal end of the sleeve includes at least one notch configured to engage a driving instrument. The rod reducing member and the sleeve are configured to longitudinally translate relative to the anchoring member. The rod reducing member may be configured to engage a spinal rod. The rod reducing member includes a ring disposed at the proximal end thereof, wherein the sleeve is configured to rotate about the ring. The anchoring member may be configured to removably attach to a bone anchor. The proximal end of the anchoring member includes at least one notch configured to engage a driving instrument. The anchoring member includes first and second arms extending distally from an anchor head. At least one of the first and second arms has a distal end configured to removably attach to the bone anchor. The internal surface of the sleeve may be configured to rotate about the external surface of the anchor head. The sleeve and the anchor head may be threadably engaged.

According to another aspect of the present disclosure, a method for providing spinal support includes providing a rod reduction device having a rod reducing member configured to engage a spinal rod; an anchoring member is configured to removably attach to a bone anchor; and a sleeve defining a longitudinal axis and being operably associated with the rod reducing member and the anchoring member, the sleeve being rotatable with respect to the anchoring member for longitudinally translating the rod reducing member, wherein the rod reducing member and the sleeve are configured to longitudinally translate relative to the anchoring member. The method further includes reducing at least one spinal rod into at least one bone anchor; adjusting the at least one spinal rod; and locking the at least one spinal rod to the at least one bone anchor. The method also includes mounting the at least one bone anchor and the at least one spinal rod to at least one vertebral body.

According to another aspect of the present disclosure, a rod reduction device includes a sleeve and a rod reducing member operably associated therewith. The sleeve defines a longitudinal axis. The sleeve may include a threaded internal surface. The sleeve includes at least one notch disposed at the proximal end thereof. The sleeve includes an annular channel extending through a distal end thereof. The sleeve has a pair of arms extending distally therefrom. Each arm has a distal end configured to engage a bone anchor. Each arm may be configured to removably attach to the bone anchor.

The rod reducing member is configured to translate along the longitudinal axis thereof in response to rotation of the sleeve about the longitudinal axis thereof. The rod reducing member is configured to engage a spinal rod for selectively reducing the spinal rod into the bone anchor. The rod reducing member includes an annular ring disposed on a proximal end thereof. The annular ring of the rod reducing member and the annular channel of the sleeve are operably associated with each other. The sleeve may be configured to rotate with respect to the annular ring.

BRIEF DESCRIPTION OF THE DRAWINGS

The above and other aspects and features of the present disclosure will become more apparent in light of the following detailed description when taken in conjunction with the accompanying drawings in which:

FIG. 6 is a perspective view of a set screw and a driving tool for the rod reduction device of FIGS. 1 and 2; and FIG. 6A is an enlarged perspective view of section 6A of FIG. 6.

DETAILED DESCRIPTION OF EMBODIMENTS

Figure 1:
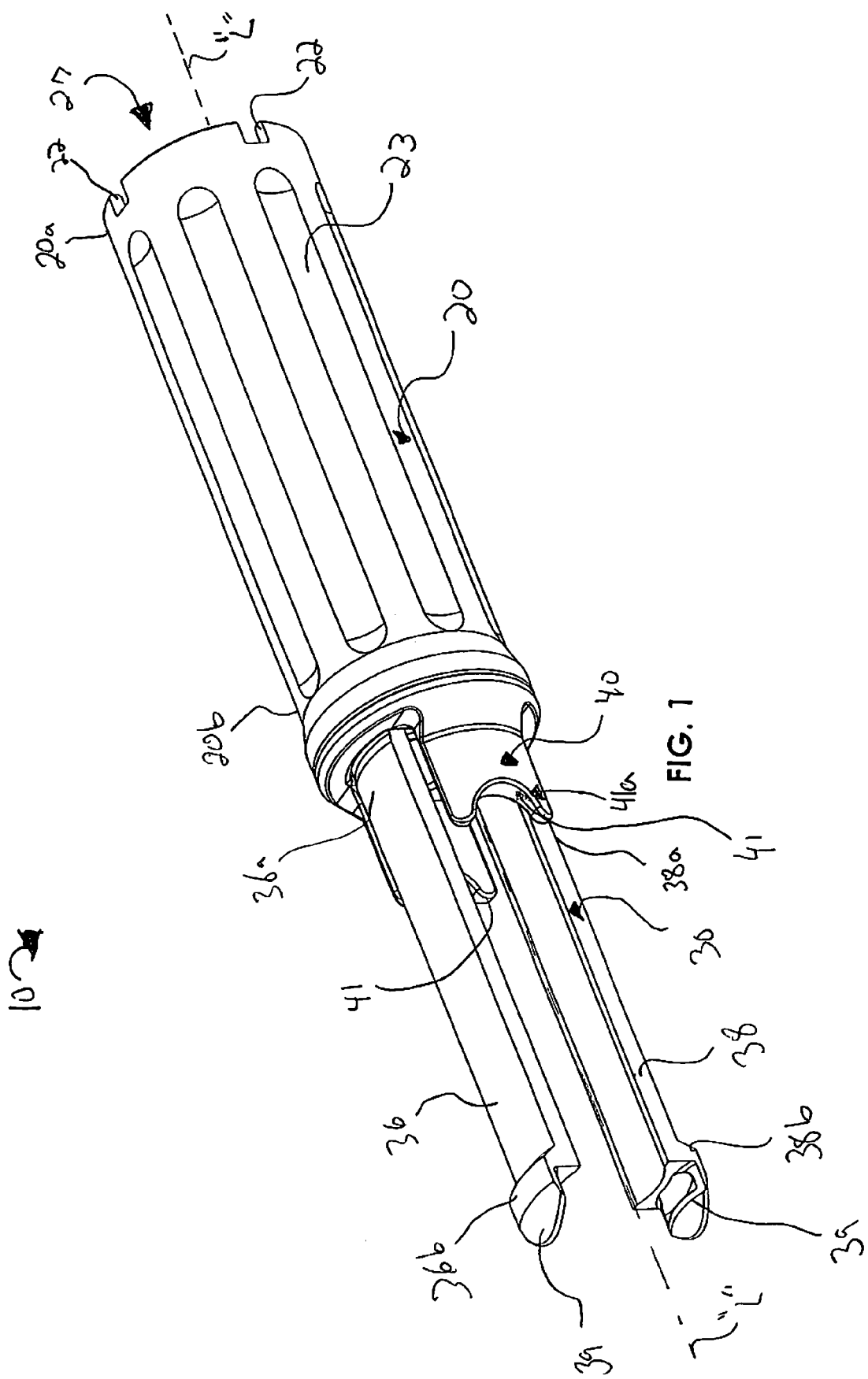
FIG. 1 is perspective view of a rod reduction device in accordance with the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates a rod reduction device 10. In accordance with the present disclosure, the rod reduction device 10 includes a sleeve 20, an anchoring member 30, and a rod reducing member 40.

Figure 2:
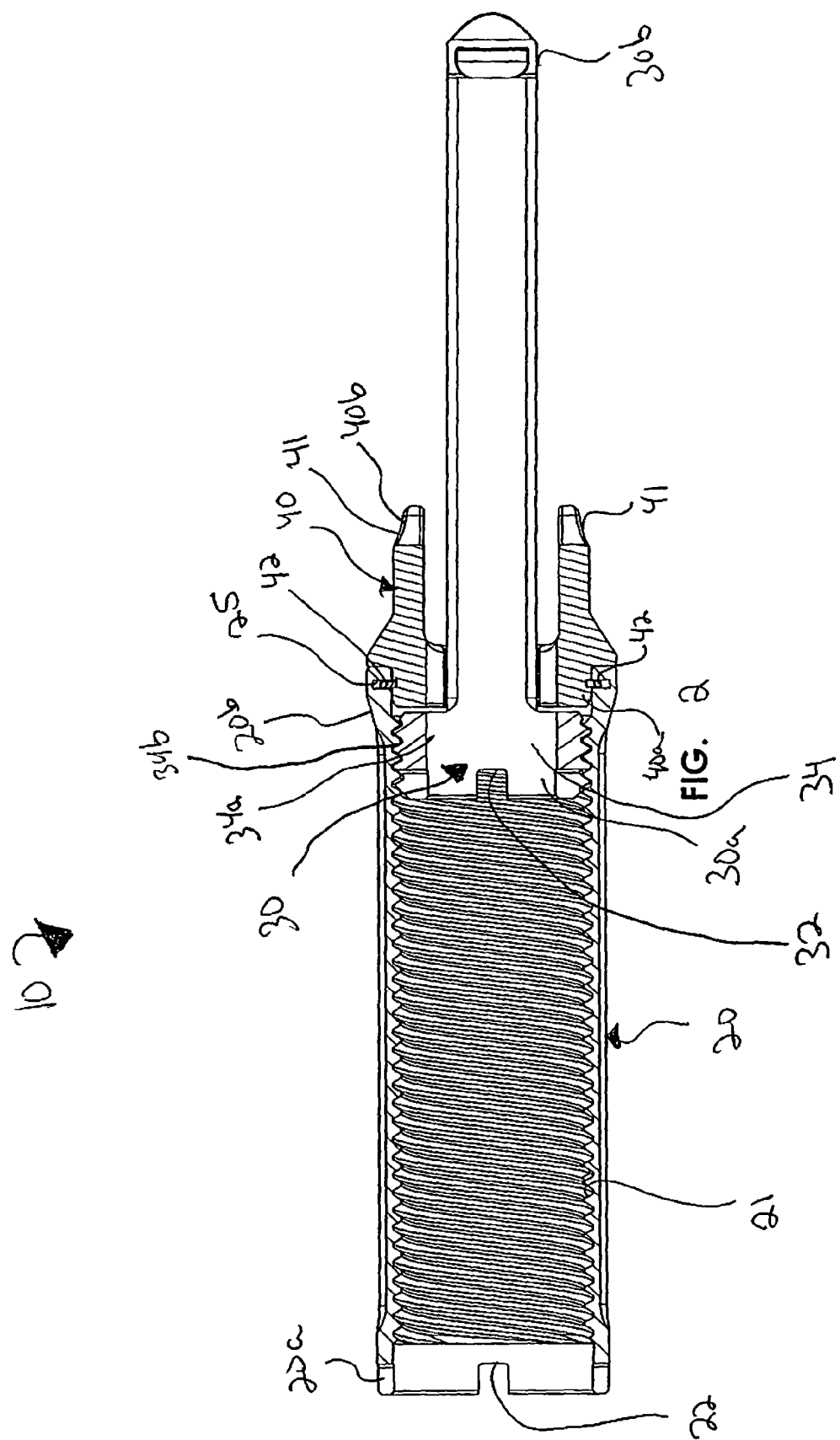
FIG. 2 is a cross-sectional view of the rod reduction device of FIG. 1.

With reference to FIGS. 1-5, the sleeve 20 defines a longitudinal axis "L" and is operably associated with the rod reducing member 40 and the anchoring member 30. The sleeve 20 includes a longitudinal passage 27, proximal and distal ends 20a, 20b, respectively, and internal and external surfaces 21, 23 (FIG. 2). The proximal end 20a of the sleeve 20 includes one or more notches 22 configured to engage a driving instrument such as a screw driver or the driving instrument 100 (described in further detail herein below) illustrated in FIGS. 3 and 4. The distal end 20b of the sleeve 20 includes an annular channel 25 (FIG. 2) for engaging the rod reducing member 40. The sleeve 20 may be movable with respect to the anchoring member 30 for longitudinally translating the rod reducing member 40 relative to anchor member 30. The sleeve 20 may be configured to rotate about axis "L" independent of the rod reducing member 40.

With continued reference to FIG. 2, the rod reducing member 40 includes proximal and distal ends 40a, 40b, respectively. The distal end 40b of the rod reducing member 40 includes one or more projecting portions 41 configured to engage a spinal rod "R" (see FIG. 3). Each projecting portion 41 includes a channel 41a (FIG. 1), which may be arcuate, extending therethrough transverse to the longitudinal axis "L" and dimensioned to engage the spinal rod "R" when the rod reducing member 40 is distally translated along the longitudinal axis "L." The rod reducing member 40 includes a ring 42 disposed at the proximal end 40a thereof for engaging the sleeve 20 and enabling the sleeve 20 to rotate thereabout. The rod reducing member 40 may be configured to translate without rotating with respect to the anchoring member 30.

Figure 3:
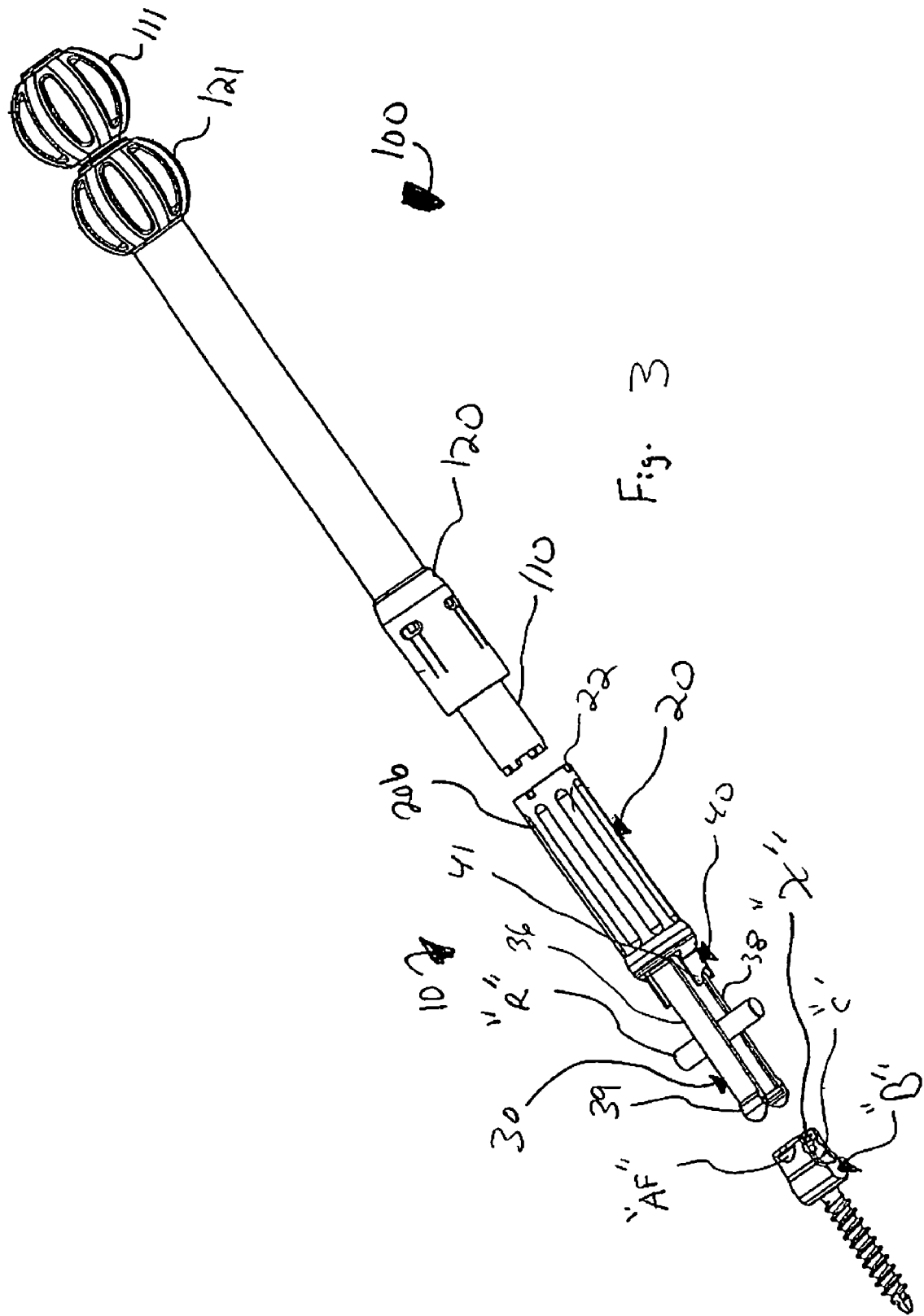
FIG. 3 is a perspective view of a rod reduction assembly with the rod reduction device of FIGS. 1-2, a spinal rod, a bone anchor and a driving instrument shown in a first position.
Figure 4:
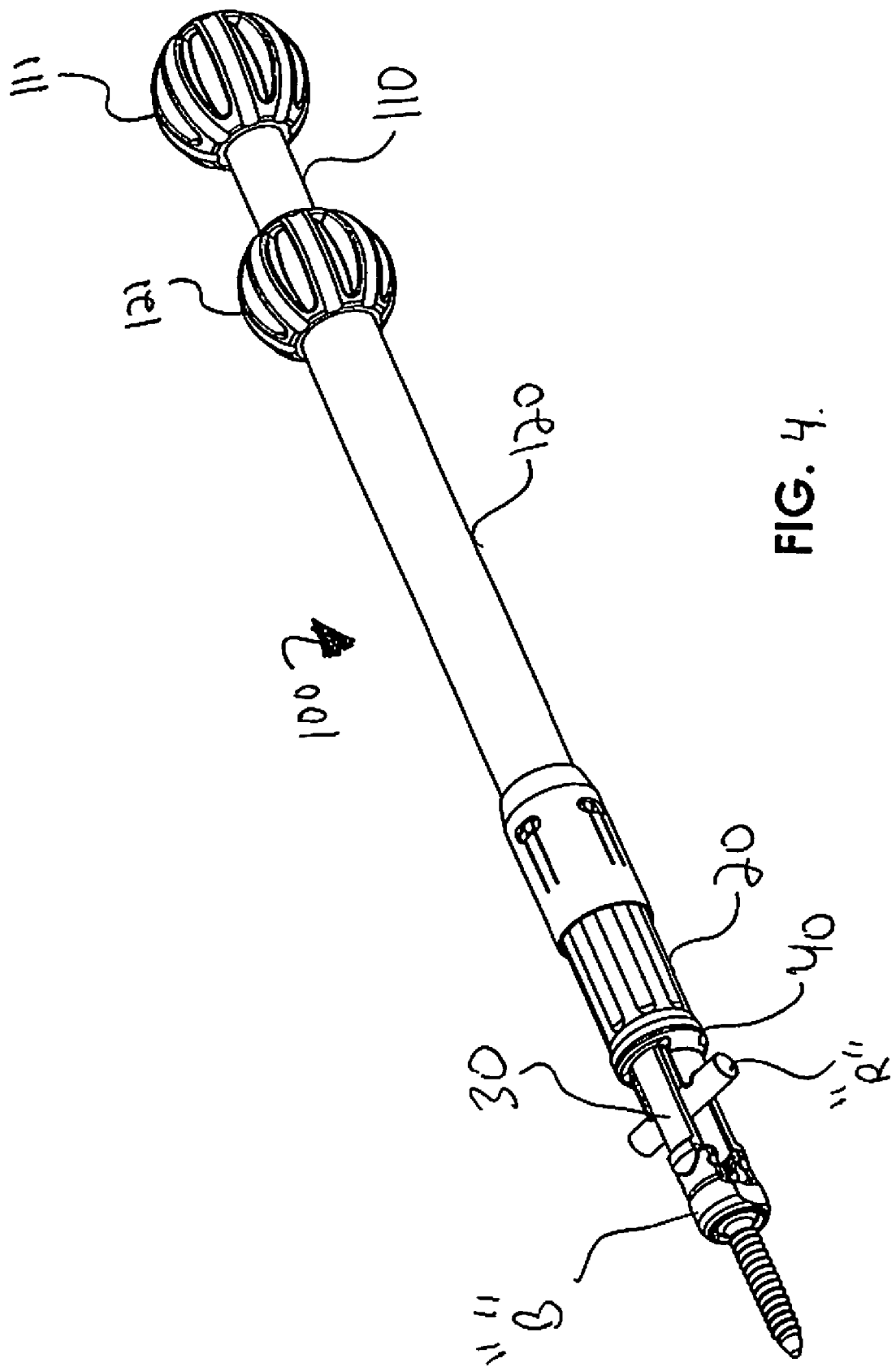
FIG. 4 is a perspective view of the rod reduction assembly of FIG. 3 with the driving instrument in one of a plurality of positions between the first position illustrated in FIG. 3 and a second position illustrated in FIG. 5.
Figure 5:
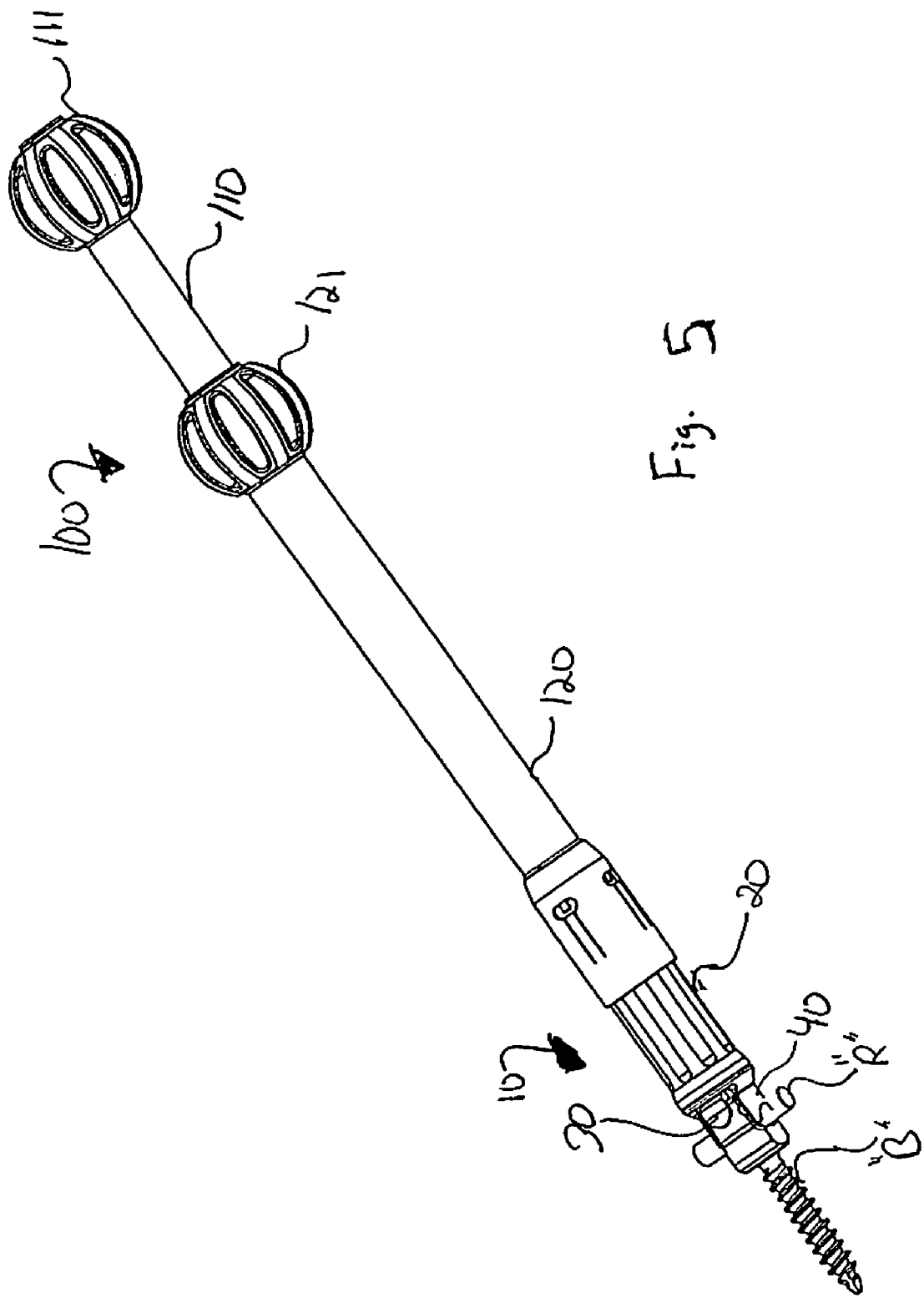
FIG. 5 is a perspective view of the rod reduction assembly of FIGS. 3-4 with the driving instrument in the second position.

Referring again to FIGS. 1-5, the anchoring member 30 includes proximal and distal ends 30a, 30b, respectively. The anchoring member 30 includes first and second arms 36, 38 extending distally from an anchor head 34 for removably attaching to a bone anchor "B" with complimentary attaching features "AF" disposed on the proximal portion of the bone anchor "B" (FIG. 3). The first and second arms 36, 38 have proximal ends 36a, 38a and distal ends 36b, 38b. Each distal end 36b, 38b may include a grasping feature 39 such as a hook or a claw. The grasping feature 39 may be configured to removably attach to the bone anchor "B" and the complimentary attaching features "AF." The anchor head 34 includes an internal surface 34a and an external surface 34b. The proximal end 30a of the anchoring member 30 includes one or more notches 32 configured to engage a screw driver or the driving instrument 100 (described in further detail herein below) illustrated in FIGS. 3-5.

With continued reference to FIG. 3, the rod reducing member 40 and the sleeve 20 are configured to longitudinally translate relative to the anchoring member 30. The sleeve 20 and the anchoring member 30 are disposed in mechanical cooperation such that they may move relative to each other. The internal surface 21 of the sleeve 20 may be threaded and may be configured to rotate about the external surface 34b of the anchor head 34, which also may be threaded. Thus, the sleeve 20 and the anchor head 34 may be threadably engaged. Notwithstanding the foregoing, the rod reduction device 10 may include any suitable translation mechanism capable of allowing longitudinally translation of the rod reducing member 40 and the sleeve 20 with respect to the anchoring member 30. For example, certain embodiments of the rod reduction device 10 may include a ratchet mechanism configured to allow longitudinal translation of the rod reducing member 40 and the sleeve 20 relative to the anchoring member 30.

Referring again to FIGS. 1-5, the rod reduction device 10 is positionable through a plurality of positions including a first position (FIGS. 1-3) and a second position (FIG. 5). The rod reduction device 10 is at its greatest length in the first position and its shortest length in the second position. The first and second arms 36, 38 of the anchoring member 30 are unconstrained and sufficiently flexible to mount onto the bone anchor "B" when the rod reduction device 10 is positioned in the first position. The first and second arms 36, 38 may be forced longitudinally over a proximal portion of the bone anchor "B" until the distal ends of the arms 36, 38 are seated and the grasping features 39 are removably attached to the complimentary attaching features "AF" disposed on the proximal portion of the bone anchor "B." Alternatively, the rod reduction device 10 may be placed alongside the bone anchor "B" with the grasping features 39 aligned with a rod receiving channel "C" of a saddle "X" of the bone anchor "B" and rotated to engage the grasping features 39 with the complimentary attaching features "AF." Rotation of the sleeve 20 in a first direction about axis "L" translates the rod reducing member 40 and the sleeve 20 distally relative to the anchoring member 30, thereby shortening the rod reduction device 10. During rotation and the shortening of the rod reduction device 10, each projecting portion 41 of the rod reducing member 40 and the first and second arms 36, 38 maintain a 90 degree offset relationship. This is due to the fact that the complimentary attaching features "AF" on the bone anchor "B" are perpendicular to the saddle "X" of the bone anchor "B." Further rotation of the sleeve 20 urges the rod reducing member 40 and the sleeve 20 distally along the first and second arms 36, 38, positioning the first and second arms 36, 38 further inside the sleeve 20. As a result, the sleeve 20 captures the first and second arms 36, 38 and prevents them from flexing or otherwise disengaging from the bone anchor "B", thereby providing an increasingly more positive attachment to the bone anchor "B."

After the rod reduction device 10 is assembled to the bone anchor "B", the sleeve 20 may be rotated about axis "L" at least a partial turn to fully engage the bone anchor "B." A screw driving instrument may be placed down the longitudinal passage 27 and into a driver receiving recess in the bone anchor "B" for driving the bone anchor "B" into bone. The entire assembly may then be introduced and placed in bone. Additional bone anchors "B" may be introduced and placed in bone at other vertebra on the same side of the spine. The bone anchor "B" may be implanted into bones with or without the spinal rods "R" attached to them.

The spinal rod "R" can be attached to the bone anchor "B" with rod reduction device 10. To this end, the spinal rod "R" is first placed between the first and second arms 36, 38 and aligned above the bone anchor "B." The sleeve 20 may then be rotated about axis "L" for driving each projecting portion 41 to contact the spinal rod "R" for reducing the spinal rod "R" into the saddle "X" of the bone anchor "B." A series of the rod reduction devices 10 may sequentially or alternately incrementally and measurably be actuated to reduce a spinal rod "R" such that the pathology and deformity can be corrected in small maneuvers rather than one large correction which may be more difficult to achieve and/or may cause damage to the spine.

Once the spinal rod "R" is fully introduced into the bone anchor "B" and no further manipulation at that level is necessary, a set screw "S" (FIGS. 6-6A) may be passed through the rod reduction device 10 by a driving tool "DT" (FIGS. 6-6A), engaged with the corresponding threads on the bone anchor housing "H", and tightened to lock the spinal rod "R" to the bone anchor "B." Removal of the rod reduction device 10 from the bone anchor "B" is then possible unless further manipulation is desired. Removal of the rod reduction device 10 is achieved by unthreading the sleeve 20 until the first and second arms 36, 38, and thus the grasping features 39, are able to separate and detach from the bone anchor "B." Alternatively, removal of the rod reduction device 10 may be achieved when the entire rod reduction device 10 is rotated 90 degrees about the longitudinal axis "L" and the rod reduction device 10 disengages from the bone anchor "B."

In an alternate approach, the bone anchor "B" may be implanted into bone prior to mounting the rod reduction device 10 thereto. The reduction of the spinal rod "R" and the insertion of the set screw "S" may be performed thereafter.

As discussed above, the driving instrument 100 (FIGS. 3-5) may also be used. The driving instrument 100 includes an inner and outer sleeve 110, 120 and is configured for attaching to the rod reducing device 10. The outer sleeve 120 engages the external surface 20b of the sleeve 20 of the rod reduction device 10 to hold the driving instrument 100 and the rod reduction device 10 together. The outer sleeve 120 includes an anti-rotation handle 121 for preventing rotation of the outer sleeve 120 and the sleeve 20 (of the rod reduction device 10) while the inner sleeve 110 is rotated with a proximal handle 111. The driving instrument 100 may be fully cannulated for enabling a set screw "S" to be passed therethrough for locking a spinal rod "R" to the bone anchor "B."

The bone anchor "B" may also be cannulated to receive a guidewire so that the distal end of the bone anchor "B" may be inserted percutaneously over the guidewire, either before or after mounting the rod reduction device 10 to the bone anchor "B."

In operation, a user may employ the rod reduction device 10 to reduce the spinal rod "R" into the saddle "X" of the bone anchor "B." The bone anchor "B" may be implanted in the bone before or after reducing the spinal rod "R" into saddle "X." The user may use any suitable instrument, such as driving instrument 100, to insert bone anchor "B" into the bone. In any event, rod reduction device 10 facilitates spinal rod reduction.

To perform the spinal rod reduction, the user initially engages the grasping features 39 of the first and second arms 38, 36 to the complimentary attaching features "AF" of bone anchor "B," thereby securing rod reduction device 10 to bone anchor "B." After fixing the bone anchor "B" to the rod reduction device 10, the user places the spinal rod "R" between the first and second arms 36, 38 and then moves the sleeve 20 and rod reducing member 40 distally relative to the anchoring member 30. During the distal motion of the sleeve 20 and the rod reducing member 30, the channels 41a engage the spinal rod "R." Continued distal advancement of the sleeve 20 and the rod reducing member 40 relative to the anchoring member 30 urges the spinal rod "R" into the saddle "X" of the bone anchor "B," reducing the spinal rod "R" to the bone anchor "B."

After reducing the spinal rod "R" into the bone anchor "B," the user passes the set screw "S" through the rod reduction 10 and into the bone anchor "B" with any suitable tool, such as driving tool "DT." The set screw "S" is then engaged with the bone anchor housing "H" and tightened to lock the spinal rod "R" to the bone anchor "B." The user then detaches the rod reduction device 10 from the bone anchor "B." To detach the rod reducing device 10 from the bone anchor "B," the user may move the sleeve 20 and the rod reducing member 40 proximally relative to the anchor member 30 to separate the grasping features 39 from the bone anchor "B." Alternatively, the user may rotate the entire rod reduction device 10 90 degrees about longitudinal axis "L" to disengage it from the bone anchor "B." A series of the rod reduction devices 10 may sequentially or alternately incrementally and measurably be actuated to reduce a spinal rod "R" such that the pathology and deformity can be corrected in small maneuvers rather than one large correction which may be more difficult to achieve and/or may cause damage to the spine.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

What is claimed is:

1. A rod reduction device, comprising:
   a rod reducing member configured to engage a spinal rod;
   an anchoring member configured to removably attach to a bone anchor;

a sleeve defining a longitudinal axis and being operably associated with the rod reducing member and the anchoring member, the sleeve being rotatable about the anchoring member for longitudinally translating the rod reducing member relative to the anchoring member; and a ring enclosed between the sleeve and the rod reducing member that facilitates the rotational movement of the sleeve around the ring and the rod reducing member to longitudinally translate the rod reducing member.

2. The rod reduction device of claim 1, wherein the sleeve rotates about the longitudinal axis of the sleeve independent of the rod reducing member.

3. The rod reduction device of claim 1, wherein the anchoring member includes first and second arms extending distally from an anchor head.

4. The rod reduction device of claim 3, wherein an internal surface of the sleeve rotates about an external surface of the anchor head and an external surface of the rod reducing member.

5. The rod reduction device of claim 3, wherein the sleeve and the anchor head are threadably engaged.

6. The rod reduction device of claim 3, wherein at least one of the first and second arms has a distal end removably attachable to a bone anchor.

7. The rod reduction device of claim 1, wherein the proximal end of the sleeve includes at least one notch configured to engage a driving instrument.

8. A rod reduction device, comprising:

a sleeve defining a longitudinal axis and having a pair of arms extending distally therefrom, each arm having a distal end that is engagable with a bone anchor;

a rod reducing member operably associated with the sleeve, wherein the rod reducing member translates along the longitudinal axis of the sleeve in response to rotation of the sleeve about the longitudinal axis of the sleeve, wherein the rod reducing member is engagable with a spinal rod for selectively reducing the spinal rod into the bone anchor; and a ring enclosed between the sleeve and the rod reducing member that facilitates the rotational movement of the sleeve to longitudinally translate the rod reducing member.

9. The rod reduction device of claim 8, wherein the sleeve includes a threaded internal surface.

10. The rod reduction device of claim 8, wherein the ring is disposed on a proximal end of the rod reducing member and the sleeve defines an annular channel within a distal end of the sleeve, wherein the ring is supported in the annular channel to facilitate rotational movement of the sleeve relative to the rod reducing member.

11. The rod reduction device of claim 10, wherein the sleeve rotates about the longitudinal axis of the sleeve with respect to the ring of the rod reducing member.

12. The rod reduction device of claim 11, wherein the rod reducing member remains rotationally stationary as the sleeve rotates about the ring of the rod reducing member.

13. The rod reduction device of claim 8, wherein the sleeve includes at least one notch disposed at the proximal end thereof.

14. The rod reduction device of claim 8, wherein the sleeve rotates around the ring and the rod reducing member.

15. The rod reduction device of claim 14, wherein the sleeve rotates about external surfaces of the ring and rod reducing member.

16. A rod reduction device, comprising:

a rod reducing member configured to engage a spinal rod;

an anchoring member configured to removably attach to a bone anchor;

a sleeve that is rotatable about the anchoring member to longitudinally translate the rod reducing member relative to the anchoring member; and a ring enclosed between the sleeve and the rod reducing member that facilitates the rotational movement of the sleeve.

17. The rod reduction device of claim 16, wherein the sleeve rotates about external surfaces of the ring and rod reducing member.

18. The rod reduction device of claim 17, wherein the ring is disposed on a proximal end of the rod reducing member and the sleeve defines an annular channel within a distal end of the sleeve, wherein the ring is supported in the annular channel to facilitate rotational movement of the sleeve relative to the rod reducing member.

* * * * *